US009427346B2

(12) United States Patent
Herbst et al.

(10) Patent No.: US 9,427,346 B2
(45) Date of Patent: Aug. 30, 2016

(54) SHUNTING OF DIETARY LIPIDS INCLUDING CHOLESTEROL

(71) Applicant: Boston Scientific Scimed, Inc., Maple Grove, MN (US)

(72) Inventors: Thomas J. Herbst, Coon Rapids, MN (US); Lynne E. Swanson, Edina, MN (US)

(73) Assignee: Boston Scientific Scimed, Inc., Maple Grove, MI (US)

( * ) Notice: Subject to any disclaimer, the term of this patent is extended or adjusted under 35 U.S.C. 154(b) by 161 days.

(21) Appl. No.: 14/201,093

(22) Filed: Mar. 7, 2014

(65) Prior Publication Data
US 2014/0276344 A1 Sep. 18, 2014

Related U.S. Application Data

(60) Provisional application No. 61/785,194, filed on Mar. 14, 2013.

(51) Int. Cl.
*A61M 5/00* (2006.01)
*A61F 5/00* (2006.01)
*A61M 27/00* (2006.01)

(52) U.S. Cl.
CPC ........... *A61F 5/0013* (2013.01); *A61F 5/0076* (2013.01); *A61M 27/002* (2013.01)

(58) Field of Classification Search
CPC . A61F 5/0013; A61F 5/0076; A61M 27/002
USPC ........................................ 604/8, 9
See application file for complete search history.

(56) References Cited

U.S. PATENT DOCUMENTS

| 5,391,143 A | 2/1995 | Kensey |
| 6,022,333 A * | 2/2000 | Kensey ............... A61M 1/1678 604/29 |
| 6,190,347 B1 | 2/2001 | Kensey |
| 8,398,577 B2 | 3/2013 | Burnett |
| 2012/0029466 A1* | 2/2012 | Callaghan ............ A61B 5/0215 604/500 |

OTHER PUBLICATIONS

Dixon, J Brandon. "Lymphatic Lipid Transport: Sewer or Subway?" Trends Endocrinol Metab. Aug. 2010; 21(8): 480-487.*
Cheng, J-T. et al., "Chyluria Presenting as Milky Urine and Nephrotic-range Proteinuria," Int. Soc. Nephrol., vol. 70, pp. 1518-1522 (2006).
Mallick, A. et al., "Disorders of the Lymph Circulation: Their Relevance to Anaesthesia and Intensive Care," vol. 91, pp. 265-272 (2003).
Takechi, R. et al., "Chylomicrom Amyloid-beta in the Aetiology of Alzheimer's Disease," *Atherosclerosis Supp.*, vol. 9, pp. 19-25 (2008).
Tomkin, G. H., "The Inestine as a Regulator of Cholesterol Homeostasis in Diabetes," *Atherosclerosis Supp.*, vol. 9, pp. 27-32 (2008).
Redgrave, T.G., "Chylomicrons in Disease-Future Challenges," *Atherosclerosis Supp.*, vol. 9, pp. 3-6 (2008).
Berg, J.M. et al., *Biochemistry*, 5th ed., Ch. 22, pp. 601-632 (2002).

* cited by examiner

*Primary Examiner* — Leslie Dark
(74) *Attorney, Agent, or Firm* — Bookoff McAndrews, PLLC

(57) ABSTRACT

Methods and devices for redirecting at least a portion of a fluid from the mesenteric lymphatic system for elimination from the body are disclosed. The fluid may be redirected for elimination through the urinary system or redirected outside the body. The methods and devices disclosed may prevent a portion of a patient's dietary lipids, including cholesterol, from being absorbed, thereby reducing the total caloric load to assist in weight management.

19 Claims, 5 Drawing Sheets

SHUNTING OF DIETARY LIPIDS INCLUDING CHOLESTEROL

CROSS-REFERENCE TO RELATED APPLICATIONS

This application claims the benefit of priority from U.S. Provisional Application No. 61/785,194, filed on Mar. 14, 2013, the entirety of which is incorporated by reference herein.

TECHNICAL FIELD

Various embodiments of the present disclosure relate generally to medical devices and related methods. More specifically, the present disclosure relates to devices and methods for redirecting a fluid from the base of the thoracic duct. Embodiments of the present disclosure may be useful in weight management, such as treatment of obesity, e.g., morbid obesity.

BACKGROUND

Weight management can be difficult for many people. Obesity is a condition where a person's body stores an excess amount of fat, and can be caused by ingesting an excess amount of calories via the alimentary tract system. Various treatments are available to treat obesity and the incidence of pathophysiology comorbidities. Those treatments include surgical procedures, e.g., obstruction or bypass modalities of the digestive system, and behavioral modification. Such treatments have at their core mechanism of action (MOA) a reduction in daily caloric load below physiologic basal maintenance needs, which for an adult male is about 2200 kcal/day (i.e., about 2200 food calories per day) and for an adult female about 1800 kcal/day (i.e., about 1800 food calories per day). MOAs leading to weight loss may include, for example, a reduction in calories ingested, decreased absorption, and/or hormonal changes that alter satiation (e.g., cause a person to feel full sooner).

There remains a need for alternative methods of achieving caloric load diminution to assist patients in weight management and improved health.

SUMMARY OF THE DISCLOSURE

The present disclosure includes methods and devices for redirecting or shunting of at least a portion of a patient's daily consumed calories to make them unavailable for intermediary metabolism, and eliminating them from the body. The present disclosure further includes methods and devices for reducing the amount of lipids such as cholesterol that are absorbed in the body.

The present disclosure includes a method of treating a patient, comprising redirecting at least a portion of a fluid from the thoracic duct to prevent lipids in the fluid, including, e.g., from being absorbed in the patient. Embodiments of the present disclosure may include one or more of the following features: the fluid may be redirected from the cisterna chyli; the fluid may be redirected by a device attached to the cisterna chyli; the device may include a flexible material, the device may include at least one control mechanism to regulate a flow of a fluid; the at least one control mechanism may include a valve; the device may include at least one anchoring mechanism; the device may be selectively sizable; or the fluid may be redirected outside the patient, e.g., via a stoma to the abdomen or excretion through the urinary system.

The present disclosure further includes a method of treating a patient, comprising redirecting at least a portion of a fluid from the thoracic duct, e.g., the inferior aspect of the thoracic duct, to the urinary tract to exit the patient's body within the urine. Embodiments of the present disclosure may include one or more of the following features: the fluid may be redirected from the cisterna chyli; the thoracic duct (e.g., a base of the thoracic duct) may be connected to the urinary tract through a fistula to redirect the fluid; the fluid may be redirected to a kidney (e.g., a renal pelvis of the kidney), a ureter, or a bladder. Alternatively, the fluid may be shunted via a fistula from the cisterna chyli to the surface of the skin for release into an ostomy bag.

The present disclosure further includes a method of treating a patient, the method comprising implanting a device to redirect at least a portion of a fluid from the thoracic duct, e.g., an inferior aspect of the thoracic duct into the urinary tract or exteriorly to the surface of the body. Embodiments of the present disclosure may include one or more of the following features: the fluid may be redirected from the cisterna chyli; the device may be implanted percutaneously, endoscopically, laparoscopically, or open abdomen; the device may be implanted through a urethra, a bladder, a femoral vein, an internal jugular vein, or a left subclavian vein; the method may further comprise administering at least one of a medication or a fluid to the patient; or the method may treat obesity in the patient. In some embodiments, for example, the device may be implanted in an antegrade fashion using a cystoscope to deliver through the urethra the bladder, a ureter and/or a renal pelvis of a kidney and exit at the superior ureter or renal pelvis to tunnel and establish direct communication fistulus tract with the cisterna chyli. Alternatively, in other embodiments, the device may be implanted via a superior approach and enter a vein that connects with a thoracic duct inlet at or around the left subclavian vein/internal jugular convergence. In still other embodiments, e.g., for patients with a challenging anatomy, a direct connection from the cisterna chyli to the skin surface could be created for release of the fluid into an ostomy bag outside the body.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

DETAILED DESCRIPTION

Biochemistry of Lipids and Long Chain Fatty Acids

Dietary lipids, including, e.g., fatty acids, monoglycerides, diglycerides, triglycerides, cholesterol, and phospholipids, undergo four major processes of assimilation starting in the gastrointestinal (GI) tract. (1) The first stage, emulsification, happens in the stomach and proximal small intestine. Once lipids are ingested and pass through the stomach, they form droplets in the small intestine. Bile acids are secreted from the gallbladder and enter the GI tract at the duodenum. Bile salts then coat and decrease the surface tension of the lipid droplets, which further reduces the size of the emulsified lipid droplets. (2) The second stage, hydrolysis, occurs in the jejunum. Pancreatic enzymes such as lipase, colipase, cholesterol esterase, and phospholipase degrade lipids in the emulsified droplets into non-esterified fatty acids, monoglycerides, cholesterol, and lysophospholipids. (3) In the third stage, micelle formation, the lipid products of the hydrolysis, combine with bile acids and phospholipids to form water-soluble micelles. (4) In the fourth stage, absorption, the micelles diffuse across the apical membrane of intestinal cells called enterocytes in the jejunum.

Figure 1:
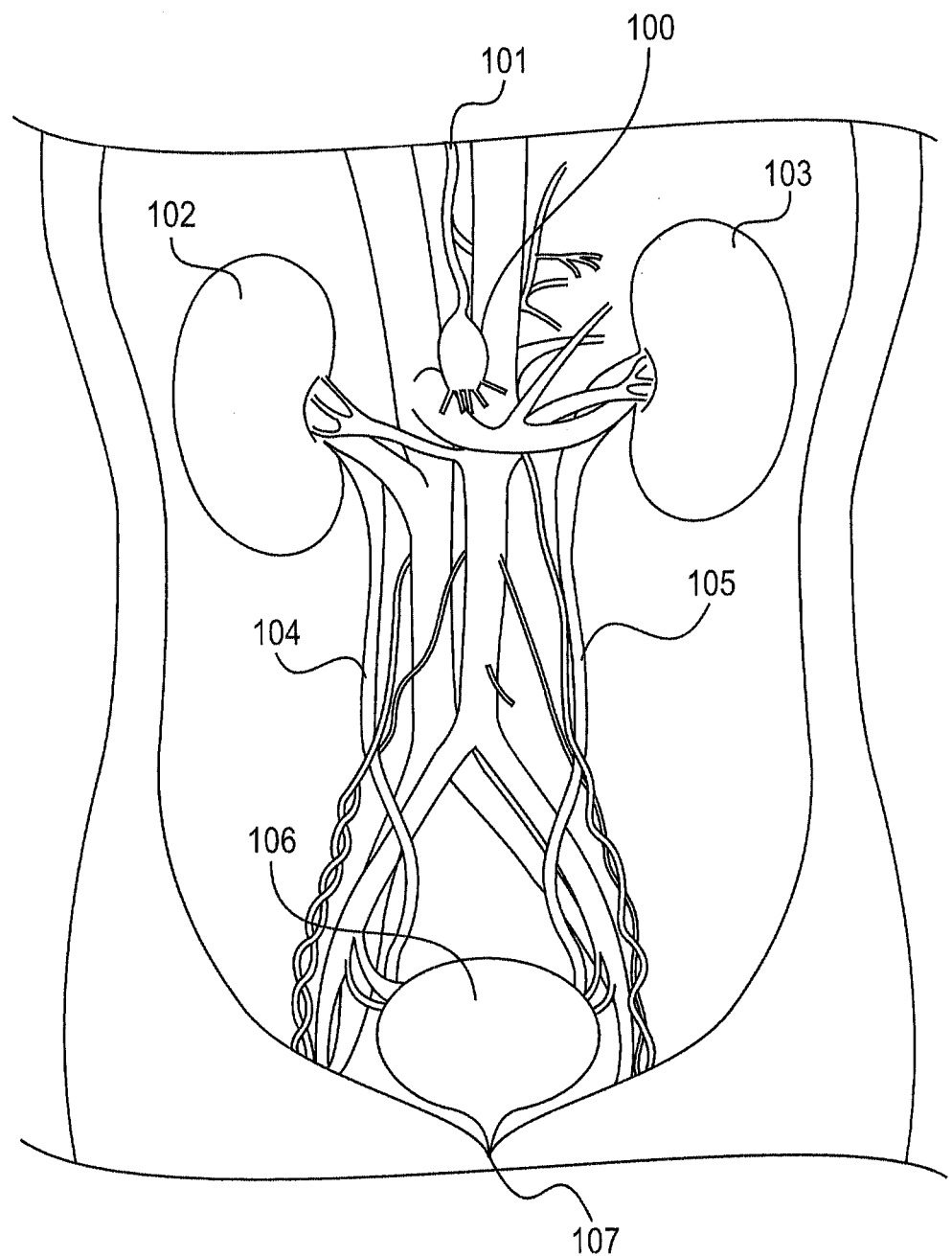
FIG. 1 shows anatomical features of the urinary and lymphatic systems.

Once inside the enterocytes of the small intestine, lipids, especially long chain fatty acids, are at least partially reprocessed and re-esterified into triglycerides and phospholipids. The esterified lipids then combine with cholesterol, other lipids, and proteins to form chylomicrons, which are "milky" lipoproteins that enable fats and cholesterol to be transported into the bloodstream. Chylomicrons transported out of the basolateral aspect of intestinal enterocytes are absorbed into lacteals, blind-end lymphatic channels present in the wall of the small intestine. Lacteals are found in the lamina propria of intestinal villi, and are contiguous with expanding lymphatic channels that drain the gut, pass through lymph nodes, and ultimately converge into a sac-like structure called the cisterna chyli (CC). The CC is located retroperitoneal to the right of the aorta and of the spine at ~T12-L1 vertebra level. While the CC is typically on the right, some data suggests it may be on the left in a small percentage of cases. The CC generally comprises thin but strong tissue, and is surrounded by superficial fibrous tissue. Histologically, the wall of the CC is similar to a medium-sized vein with collagenous, elastic, and sparse smooth muscle composition. Endothelial cells line the lumen and a prominent internal elastic lamina is present. The size and shape of the CC may vary considerably from patient to patient. In some patients, for example, the CC is little more than a convergence of the lymphatic trunks with a minimal sac-like dilation. As shown in FIG. 1, the thoracic duct 101 emanates from the superior aspect of the CC 100 and ascends the thoracic cavity along the right lateral spine, where it crosses to the left lateral spine and carries the lipid-laden high-calorie chylomicrons into venous circulation at the left subclavian vein-internal jugular vein confluence (left venous angle).

According to embodiments of the present disclosure, a lipid-rich fluid may be redirected or shunted from the lymphatic system to prevent absorption in the body. For example, at least a portion of a fluid may be removed from the CC and redirected for elimination from the body circumventing transport to the bloodstream. The fluid may be redirected and eliminated via the urinary system, or may also be removed from the body directly from the CC, e.g., via a stoma.

According to some embodiments of the present disclosure, the fluid may be redirected from the CC to the urinary tract via a fistula. FIG. 1 shows the posterior abdominal cavity and structures in the retroperitoneal space. For illustration purposes, the CC 100 is shown in FIG. 1 in front of the inferior vena cava (IVC) and aorta; in reality the CC is located behind the IVC and just right lateral to the abdominal aorta at approximately T12-L1. The lymphatic system draining the gut is schematically represented as small connecting vessels on the bottom of the CC sac. FIG. 1 shows the CC 100 and thoracic duct 101, as well as the urinary system, including the right and left kidneys 102, 103, the right and left ureters 104, 105, the bladder 106, and the urethra 107. In the urinary tract, the kidneys 102, 103 extract bodily waste for removal as urine, which passes through ureters 104, 105 into the bladder 106 for excretion through the urethra 107. By redirecting a portion of a lipid-rich fluid from the CC into the urinary tract, e.g., via a kidney (e.g., a renal pelvis or calyx of the kidney), a ureter, or the bladder, lipids may be combined with and eliminated with urine to reduce a patient's overall caloric load.

Figure 2A:
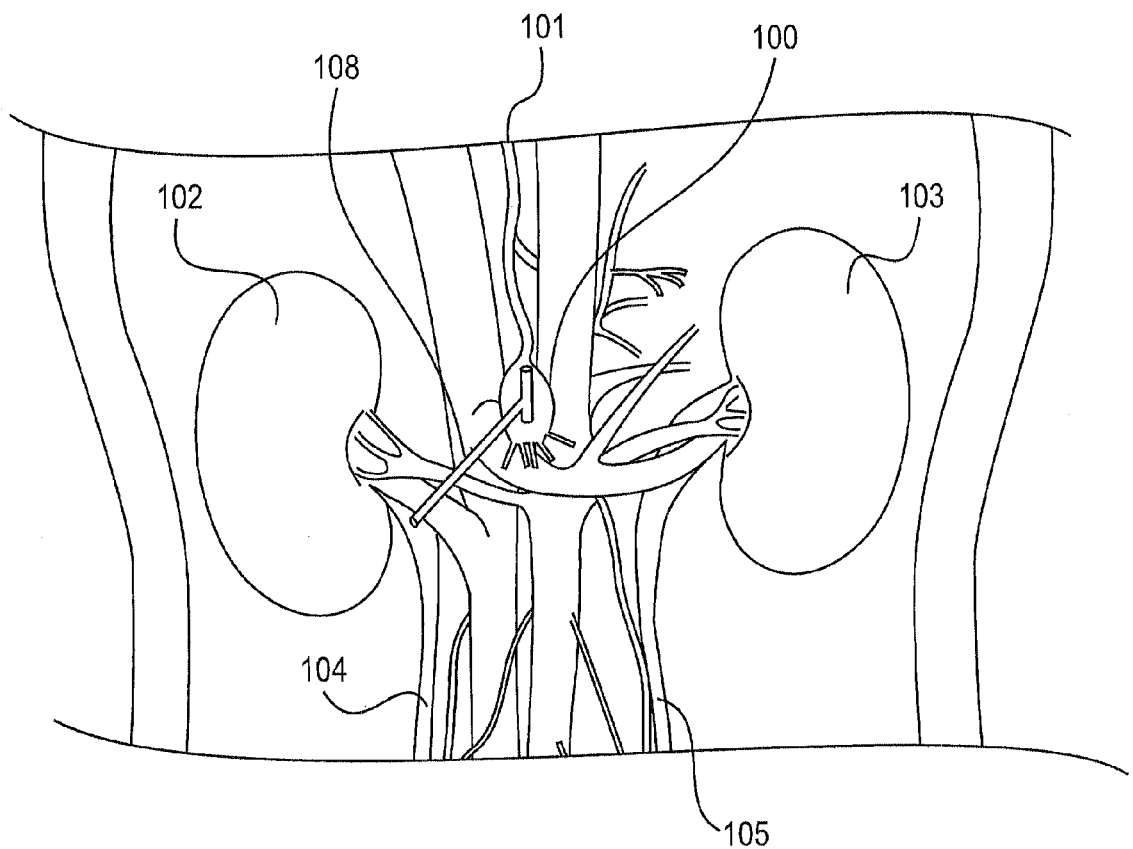
FIGS. 2A-2C illustrate exemplary embodiments of the present disclosure.

In one embodiment of the present disclosure illustrated in FIG. 2A, for example, the CC 100 may be connected to the right ureter 104 with device 108. Tissues of the CC 100 and of the right ureter 104 may be joined via a fistula connection with device 108. The device 108 extends from a proximal end located within the CC through a side port leading to a distal end located within the right ureter 104. While FIG. 2A shows a fistula at or near the right renal pelvis, it is understood that the fistula may be established at any location along ureter 104. A fistula tract between the CC 100 and the left ureter 105 is also possible and encompassed by the present disclosure.

Figure 2B:
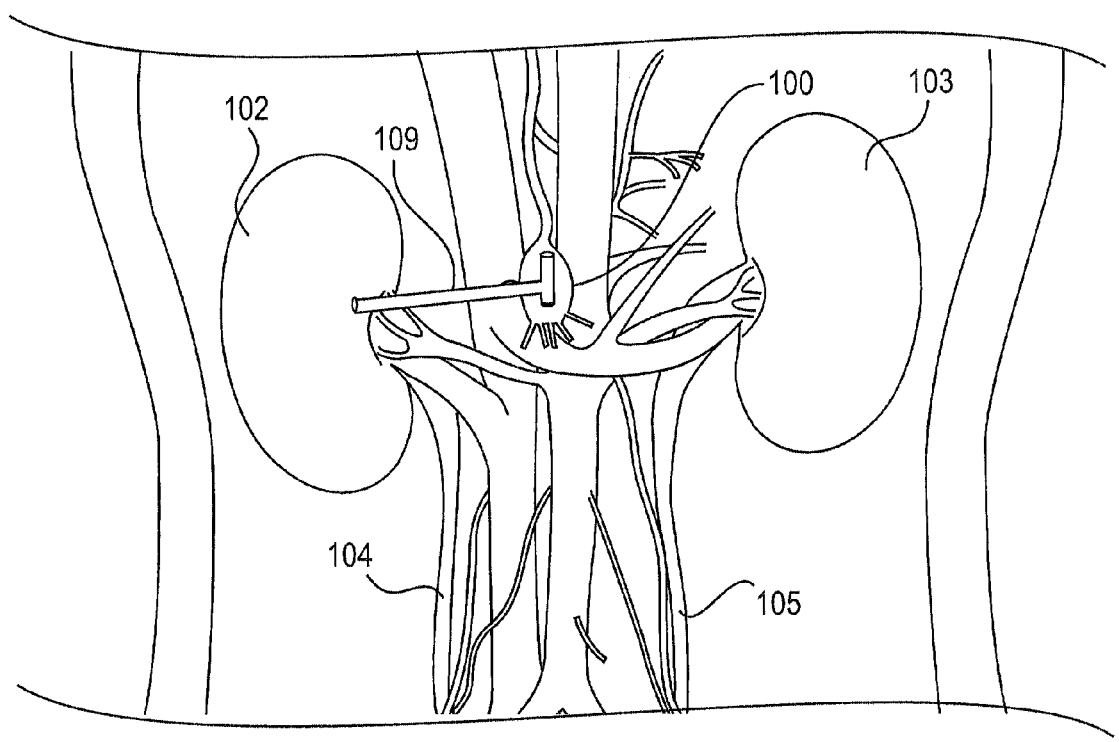

In another embodiment illustrated in FIG. 2B, the CC 100 may be connected to the right kidney 102 with device 109. The device 109 extends from a proximal end located within the CC through a side port leading to a distal end located within the renal pelvis of the right kidney 102. A person of ordinary skill in the art would understand that a fistula could also join the CC 100 and the left kidney 103 at similar anatomic junctions (e.g., the renal pelvis or calyx).

Figure 2C:
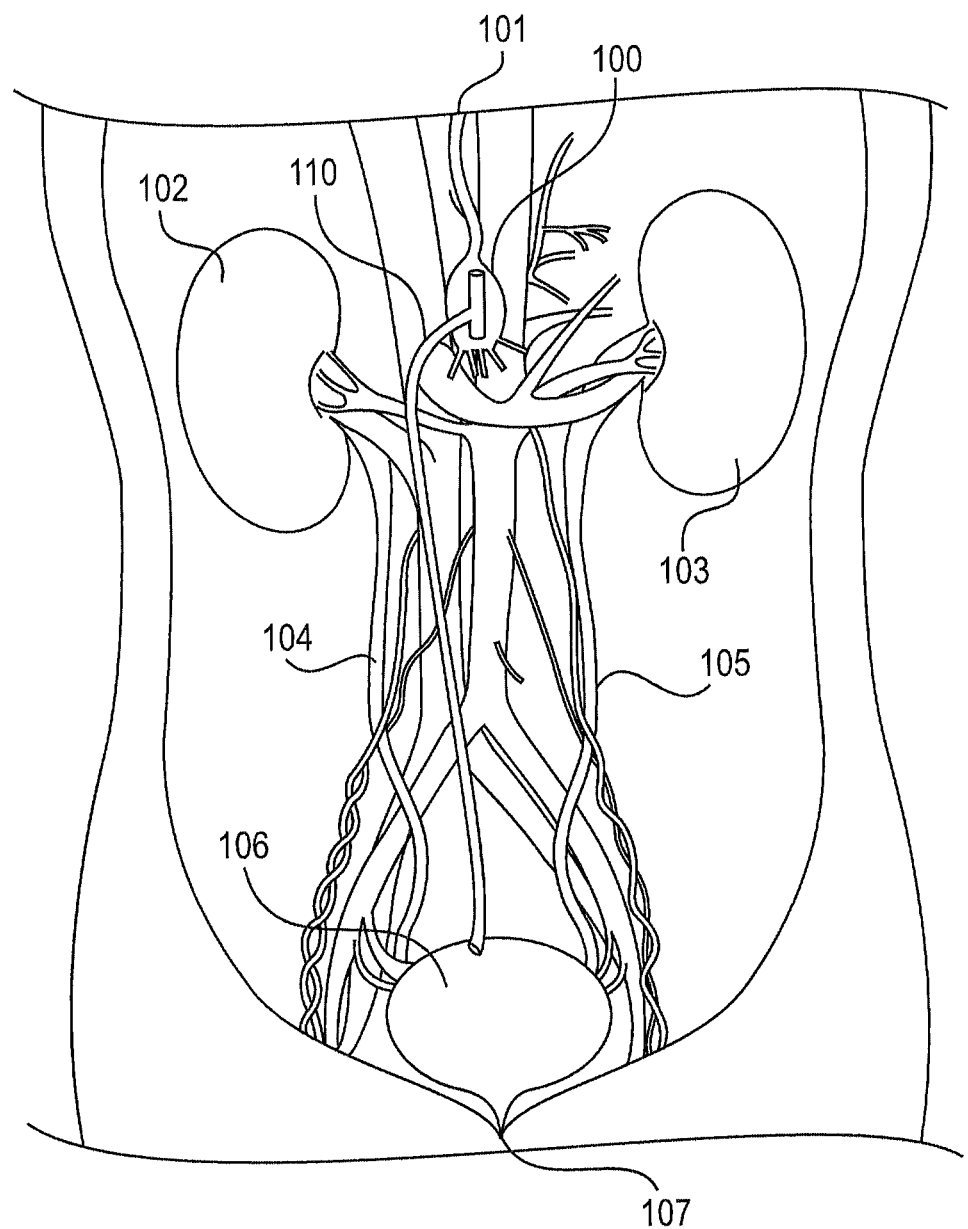

FIG. 2C shows yet another embodiment, wherein the CC 100 is connected to the bladder 106 with device 110. The device 110 extends from a proximal end located within the CC through a side port leading to a distal end located within the bladder 106. Devices 108, 109, 110 shunt at least a portion of lipid-rich fluid from the CC 100 into the urinary tract. Once in the urinary tract, resorption of the lipids is prevented by the highly elastic and leak-proof urothelium, which serves as a conduit to excrete unused lipids such as cholesterol with urine. This elimination may result in diminished calorie load and weight loss over time. In some embodiments of the present disclosure, there may be multiple connections to redirect a fluid from the CC, e.g., any combination of connections between the CC and left and right kidneys, left and right ureters, the bladder, and outside of the body.

Other embodiments consistent with the present disclosure may be contemplated. For example, a ureter may be severed and the portion of the ureter leading to the bladder anastomosed directly to the CC, such as via a vascular graft tube or other suitable device. This type of connection may be relatively more appropriate for patients with a dysfunctional kidney, wherein severing the ureter from the dysfunctional kidney may implicate fewer health concerns. A second vascular conduit may be created to anastomose the remaining ureter stub (i.e., the portion leading from the kidney) to the other ureter.

Devices

Figure 3A:
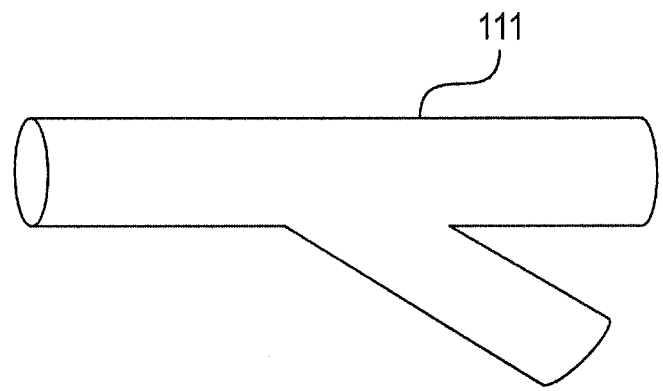
FIGS. 3A and 3B show examples of devices according to embodiments of the present disclosure.

Any suitable device for creating a fistula may be used. In some embodiments, the device has a tubular structure including one or more lumens. FIGS. 2A-2C show different 3-way, T-bone type of shunting devices 108, 109, 110, similar to another exemplary 3-way shunting device 111 shown in FIG. 3A. Each of these devices 108-111 has three legs; two legs anchoring the device in the CC 100 and a third leg emanating from a side of the lumen defined by the two legs. The device need not be limited to a 3-way configuration, however. Further non-limiting examples of devices suitable for the present disclosure include 2-way devices, 4-way devices, e.g., H-shaped device 112 shown in FIG. 3B, and the like as known to one of skill in the art. A 2-way device may simply include a cylindrical-shaped tube, for example.

The type of device chosen may include consideration for the type of tissues and strength of tissues to be joined, suitable means for attaching the device to tissue, the amount of time the device is expected to remain in the patient (e.g., short-term vs. long-term), and/or the particular needs of a patient. The device may be size-selectable and customizable, thus accommodating variability among patients' anatomy. Similarly, the size of the device lumen(s) may vary according to the needs of the patient and decision by the patient's physician or other healthcare provider.

The device may comprise a biocompatible and/or flexible material. Exemplary materials include, but are not limited to, silicone (e.g., silicone rubber or medical grade silicone), one or more polymers such as styrene-isobutylene-styrene (SIBS), polypropylene, polyurethane, or a fluoropolymer, and metals including, e.g., in the form of coils, magnets, and/or braided wire. In some embodiments, the device may include flexible inner coils or coaxial coils optionally coated with a polymer coating such as GORE™ PTFE-covered coils. The device may be flexible, for example including flexible scaffolding. Device 110 of FIG. 2C includes, for example, a flexible portion joining the CC 100 to the bladder 106.

Further, the device may include a bioresorbable material that dissolves or erodes over time. For example, in some embodiments, at least a portion of the device includes a bioresorbable material that dissolves over a predetermined time, such as from several days or weeks to several months. In some embodiments, substantially all of the device may be bioresorbable. In some embodiments, the device may include a material that permits tissue ingrowth. The material may be arranged in a scaffolding to permit tissue ingrowth along and/or inside of the device, such as at the point of attachment to a tissue surface or anchoring to a tissue wall. In some embodiments, the device may include both a bioresorbable material and a material that permits tissue ingrowth such that tissue supports the fistula as the bioresorbable material erodes over time. Such devices may, for example, be suitable for short-term implantation and remove a need to surgically remove the device. The device may also include a tissue graft, e.g., human, animal, or man-made tissue. One or more stents may also be used to support and/or expand a fistula connection according to the present disclosure including, e.g., covered stents, Nitinol stents, or plastic stents.

The device may further include a pharmaceutical drug or other therapeutic agent for release in the body. Delivery of the pharmaceutical or therapeutic agent may be effected, for example, through a porous material of the device, or embedding the pharmaceutical or therapeutic agent in a bioresorbable material of the device to be released over time.

Anchoring Mechanism

In some embodiments, the device includes at least one anchoring mechanism. The anchoring mechanism may include one or more means of attaching the device to a tissue surface wall. The anchoring mechanism may also assist in anastomosis, for example, and/or securing the device in the body for short-term or long-term implantation. In some embodiments, the anchoring mechanism may include use of one or more materials for attaching or sealing the device to a tissue surface. Examples of anchoring mechanisms include, but are not limited to, staples, sutures, a flange/flared configuration at the end of one or more legs, a grafting surface, fibrin sealants, hydrogel matrices, extended tines, magnets, or any other means of connecting two body organs.

In some embodiments, the device includes one or more flared openings to assist in anchoring the device within the CC and/or kidney, ureter, or bladder. For example, in some embodiments, the fistula may adhere to the exterior tissue surface of the organ, while in other embodiments, the fistula adheres inside of the organ. Further, the device may have a linear portion disposed within the CC, kidney, ureter, and/or bladder having sufficient length to keep the device in place. A junction between the device and the tissue surface (e.g., an inner and/or outer surface) may be sealed with a suitable material such as a fibrin sealant or hydrogel. In some embodiments, at least a portion of the device in contact with the tissue surface may include a mesh material to facilitate sealing the device to the tissue surface.

In some embodiments, the device may include two magnets. For example the device may include a first magnetic portion coupled to the wall of the CC and a second magnetic portion coupled to ureter, kidney (e.g., renal pelvis) or bladder, wherein connecting the two magnetic portions creates a fistula connection. Each magnetic portion may be separately introduced for implantation, e.g., via antegrade delivery through the urethra and retrograde delivery through a vein, or also may be introduced together for implantation. The first and/or second magnetic portions may include a magnet disposed circumferentially around a lumen through which a fluid may flow, e.g., a hollow magnet tube. In some embodiments, for example, a magnet tube may be attached to a tissue surface, wherein an opening in the tissue surface is created by perforating through a portion of tissue adjacent to the inner lumen of the magnet tube.

FIGS. 2A-2C show devices 108, 109, and 110 with a proximal longitudinal portion (e.g., a leg) disposed within the CC to assist in anchoring. In case the device establishes a passageway from the CC to outside of the body (ostomy), the device may include an anchoring mechanism to secure the device to the body surface and accordingly allow fluid to flow from the CC to exit the body into an appropriate receptacle that can be removed and replaced. The anchoring mechanism may further include a locking mechanism to lock the device to the body surface to secure it in place.

Control Mechanism

Figure 3B:
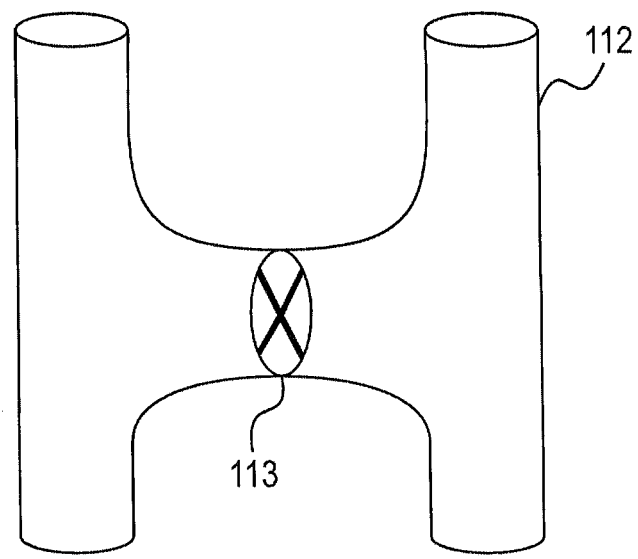

The device may include at least one control mechanism to regulate fluid flow, illustrated in FIG. 3B as control mechanism 113 of device 112. The control mechanism may regulate a fluid flow mechanically, electronically, osmostically, and/or ionically, and may also be configured for active control (e.g., to enable a patient, healthcare provider, software program or application, etc., to adjust fluid flow) or passive control (e.g., a rate of fluid flow depending on pressure and/or design of the control mechanism). For example, an electronic control mechanism may be adjusted or controlled remotely, for example by a physician or other healthcare provider via a remote or mobile device. In some embodiments, the control mechanism regulates the amount of caloric loss of a patient.

The control mechanism may include an inorganic or organic biocompatible material, such as a polymer, a metal, or human or non-human tissue. In some embodiments, the control mechanism includes a valve. Non-limited examples of control mechanisms that may be used according to the present disclosure include slitted valves, duckbill valves, apertures (e.g., a small aperture to restrict flow), elastomeric valves, one-way valves, and lumens having an hour-glass shape. In some embodiments, for example, the device includes a plurality of perforations or holes to direct and facilitate flow of a fluid from the CC into a lumen of the device. The holes may range from about 100 microns to about 500 microns, and may assist in controlling or regulating a fluid flow rate.

The control mechanism may be located at various positions within the device, such as at or near an opening or end of the device, or at any location between openings. In some embodiments, the device may include more than one control mechanism, for example two, three, or more control mechanisms.

Redirecting a fluid according to the methods presently disclosed may be continuous or may also be intermittent. For example, the device may include one or more control mechanisms configured to allow for on/off control of a fluid flow. The control mechanism(s) may include, for example, a sensor to detect the amount of fluid present and means for increasing, decreasing, initiating, and/or terminating flow through the device. In some embodiments, the control mechanism may temporarily block fluid communication through the device.

Surgical Intervention

The device may be implanted percutaneously, endoscopically, laparoscopically, or open abdomen. The device may be configured for short-term or long-term implantation. In at least some embodiments of the present disclosure, implantation of the device is reversible, i.e., the device can be removed.

In one embodiment, for example, the device is introduced through a catheter via the left subclavian vein and advanced through the thoracic duct to reach the CC. An incision may made in the wall of the CC, allowing the distal end of the device (e.g., a side port extending from the proximal end of the device as shown in FIGS. 2A-2C) to extend outside the CC while the proximal end of the device remains inside the CC. A guide tract may then extend from the side port of the device to enter the ureter, e.g., right ureter or left ureter. The device is subsequently anchored to tissue at the proximal and/or distal end with an anchoring mechanism to create the fistula. Other percutaneous methods of delivery may also be contemplated, such as implantation through a femoral vein or an internal jugular vein.

The device may also be implanted via retrograde delivery through the bladder. In such embodiments, the device is introduced through a catheter via the urethra through the bladder. Depending on whether the fistula is established between the bladder, ureter, or kidney, the device may be further advanced in order to create the fistula. For example, in some embodiments, the device is implanted endoscopically by passing through the bladder into the right ureter. The ureter wall may be pierced and the tissues anastomosed to the CC. This approach may leave the distal end of the device in the ureter for potential removal later.

In other embodiments, the device may be implanted laparscopically or via open abdomen with or without ultrasound guidance. For example, a passageway may be established from the body surface to the CC and the device secured via a circular mesh region at each end that can be fixed to the tissue with an adhesive, a fibrin sealant, a hydrogel material, or extension tines, or may also be stapled to the tissue. In some embodiments, the device includes flexible inner coils or coaxial coils coated with a GORE™ PTFE coating. Additional methods of implantation suitable for the present disclosure will be known to those of ordinary skill in the art.

Suitable imaging may be used to assist in placement of the device. For example, the device may include a material, e.g., radiopaque material, that is visible by fluoroscopy to assist in implanting the device in a desired location. Further, digital radiographs may assist in post-operative placement, maintenance, and/or monitoring of the device.

Supplemental Treatment

Elimination of fat in the urine may be painful, for example causing hypoproteinemia, edema, nausea, vomiting, diarrhea, abdominal pain, and/or backaches. Lymph fluid comprises albumin, globulins and fibrinogen, for example, such that loss of chyle in the urine may lead to a loss of protein. A patient may also develop a clot. In some cases, for example, chyle may form a clot, potentially leading to renal colic or bladder colic. Accordingly, some embodiments of the present disclosure include lifestyle changes such as changes in diet and/or fluid intake. In some embodiments, a patient may be prescribed a treatment regime following implantation of the device. For example, a physician or other healthcare provider may prescribe a medication, such as an analgesic, to alleviate pain. Other medications may be prescribed to facilitate or otherwise assist in breaking down lipids in the urine, or to facilitate or increase flow (e.g., use of a diuretic such as furosemide). The patient may also be advised how to dilute the urine to alleviate potential pain, such as ingesting fluids to break down and/or dilute lipids before excretion in the urine in order to avoid pain. Alternatively or in addition, the patient may be advised to follow a low-fat and/or high-protein diet. A high-protein diet may, for example, help to compensate for a loss of protein, e.g., due to hypoproteinemia and/or following the formation of a clot.

Other embodiments of the present disclosure will be apparent to those skilled in the art from consideration of the specification and practice of the embodiments disclosed herein. It is intended that the specification and examples be considered as exemplary only, with a true scope and spirit of the present disclosure being indicated by the following claims.

We claim:

1. A method of treating a patient, comprising:
   introducing a device into a vasculature of the patient, the device having a first end and a second end;
   advancing the device from the vasculature into a thoracic duct of the patient;
   extending the second end of the device through a wall of a cisterna chyli and then through a wall of a kidney, a ureter, or a bladder of the patient to create a fistula between the cisterna chyli and a urinary tract of the patient;
   attaching a portion of the device proximate the first end of the device to the wall of the cisterna chyli; and
   attaching a portion of the device proximate the second end of the device to the wall of the kidney, the ureter, or the bladder;
   wherein the device bypasses the vasculature to redirect at least a portion of a fluid from the thoracic duct to the urinary tract to prevent lipids in the fluid from being absorbed in the patient.

2. The method of claim 1, wherein the fluid is redirected from the cisterna chyli to a renal pelvis of the kidney to exit the patient via the urinary tract.

3. The method of claim 1, wherein an inlet of the device is disposed within the cisterna chyli and an outlet of the device is disposed within the kidney, the ureter, or the bladder.

4. The method of claim 1, wherein the device includes a flexible material.

5. The method of claim 1, wherein the device includes at least one control mechanism comprising a valve to regulate a flow of the fluid.

6. The method of claim 1, wherein the device includes at least one anchoring mechanism for securing the device to at least one of the wall of the cisterna chyli or the wall of the kidney, the ureter, or the bladder.

7. The method of claim 1, wherein a size of the device is customized to an anatomy of the patient.

8. The method of claim 1, wherein all of the fluid that enters the device is redirected outside the patient via the urinary tract.

9. The method of claim 1, wherein at least one of a first end or a second end of the device is flared, and wherein a junction between the device and at least one of the wall of the cisterna chyli or the wall of the kidney, the ureter, or the bladder is sealed with a material.

10. A method of treating a patient, comprising:
  introducing a device into a thoracic duct of the patient, the device comprising an inlet and an outlet;
  advancing a portion of the device through a wall of a cisterna chyli, such that the inlet is disposed within the cisterna chyli and the outlet is disposed in a kidney, a ureter, or a bladder of the patient; and
  redirecting at least a portion of a fluid from the thoracic duct through the wall of the cisterna chyli to the urinary tract via the device while the inlet of the device is disposed within the cisterna chyli, so that the portion of the fluid bypasses a vasculature of the patient to exit the patient's body with urine.

11. The method of claim 10, wherein the device includes at least one control mechanism between the inlet and the outlet to regulate a flow of the fluid between the cisterna chyli and the kidney, the ureter, or the bladder.

12. The method of claim 11, wherein the fluid is redirected to a renal pelvis of the kidney.

13. The method of claim 11, wherein the at least one control mechanism is located near the inlet of the device.

14. A method of treating a patient, the method comprising:
  implanting a device to create a fistula between a base of a thoracic duct and a urinary tract of the patient; and
  redirecting at least a portion of a fluid from the thoracic duct through the device to the urinary tract;
  wherein all of the fluid that enters the device bypasses a vasculature of the patient and is redirected to the urinary tract; and
  wherein an inlet of the device is disposed within a cisterna chyli of the patient while redirecting the fluid to the urinary tract.

15. The method of claim 14, wherein the device is implanted percutaneously, endoscopically, laparoscopically, or via open abdomen.

16. The method of claim 15, wherein the device is implanted through a urethra, a bladder, a femoral vein, an internal jugular vein, or a left subclavian vein.

17. The method of claim 14, further comprising administering at least one of a medication or a fluid to the patient.

18. The method of claim 14, wherein the method treats obesity in the patient.

19. The method of claim 14, wherein the device includes at least one anchoring mechanism that secures a portion of the device to a wall of the cisterna chyli.

* * * * *